(12) United States Patent
Askem et al.

(10) Patent No.: US 10,898,388 B2
(45) Date of Patent: Jan. 26, 2021

(54) REDUCED PRESSURE APPARATUSES AND METHODS

(71) Applicant: Smith & Nephew PLC, Watford (GB)

(72) Inventors: Ben Alan Askem, East Yorkshire (GB); John Philip Gowans, Hessle (GB); Allan Kenneth Frazer Grugeon Hunt, Beverley (GB)

(73) Assignee: Smith & Nephew PLC, Watford (GB)

( * ) Notice: Subject to any disclaimer, the term of this patent is extended or adjusted under 35 U.S.C. 154(b) by 433 days.

(21) Appl. No.: 15/569,596

(22) PCT Filed: Apr. 26, 2016

(86) PCT No.: PCT/EP2016/059329
§ 371 (c)(1),
(2) Date: Oct. 26, 2017

(87) PCT Pub. No.: WO2016/174048
PCT Pub. Date: Nov. 3, 2016

(65) Prior Publication Data
US 2018/0296397 A1 Oct. 18, 2018

Related U.S. Application Data

(60) Provisional application No. 62/153,483, filed on Apr. 27, 2015, provisional application No. 62/154,078, filed on Apr. 28, 2015.

(51) Int. Cl.
| | | |
|---|---|---|
| A61F 13/02 | (2006.01) | |
| A61F 13/00 | (2006.01) | |
| A61M 1/00 | (2006.01) | |

(52) U.S. Cl.
CPC .... *A61F 13/0216* (2013.01); *A61F 13/00068* (2013.01); *A61F 13/0206* (2013.01);
(Continued)

(58) Field of Classification Search
CPC .......................... A61F 13/0216; A61M 1/009
(Continued)

(56) References Cited

U.S. PATENT DOCUMENTS

| | | |
|---|---|---|
| 3,874,387 A | 4/1975 | Barbieri |
| 4,224,941 A | 9/1980 | Stivala |

(Continued)

FOREIGN PATENT DOCUMENTS

| | | |
|---|---|---|
| CN | 201664463 U | 12/2010 |
| DE | 198 44 355 | 4/2000 |

(Continued)

OTHER PUBLICATIONS

International Search Report and Written Opinion, re PCT Application No. PCT/EP2016/059329, dated Jul. 14, 2016.

(Continued)

*Primary Examiner* — Andrew J Mensh
(74) *Attorney, Agent, or Firm* — Knobbe, Martens, Olson & Bear, LLP

(57) ABSTRACT

Disclosed embodiments relate to apparatuses for wound treatment. In certain embodiments, a negative pressure wound therapy apparatus includes one or more electronic components configured to be incorporated into layers of the wound dressing or integrated on top of the wound dressing. In some embodiments, a negative pressure source is incorporated into the wound dressing. The negative pressure source can be sealed between two moisture vapor permeable cover layers or enclosed in a moisture vapor permeable pouch, and may be received in a recess of an absorbent layer or spacer layer of a wound dressing apparatus.

16 Claims, 15 Drawing Sheets

(52) U.S. Cl.
CPC .......... *A61M 1/009* (2014.02); *A61M 1/0056* (2013.01); *A61M 1/0066* (2013.01); *A61F 13/0209* (2013.01); *A61F 2013/0028* (2013.01); *A61F 2013/00268* (2013.01); *A61F 2013/00319* (2013.01); *A61M 1/0052* (2014.02); *A61M 2205/0205* (2013.01); *A61M 2205/3337* (2013.01); *A61M 2205/3344* (2013.01); *A61M 2205/42* (2013.01); *A61M 2205/8206* (2013.01)

(58) Field of Classification Search
USPC ........................................................ 604/319
See application file for complete search history.

(56) References Cited

U.S. PATENT DOCUMENTS

| | | |
|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,216,651 B2 | 5/2007 | Argenta et al. |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,776,028 B2 | 8/2010 | Miller et al. |
| D625,422 S | 10/2010 | Arbesman et al. |
| 7,837,673 B2 | 11/2010 | Vogel |
| 7,838,717 B2 | 11/2010 | Haggstrom et al. |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,062,273 B2 | 11/2011 | Weston |
| 8,080,702 B2 | 12/2011 | Blott et al. |
| 8,092,441 B2 | 1/2012 | Sugito |
| 8,118,794 B2 | 2/2012 | Weston et al. |
| 8,158,844 B2 | 4/2012 | McNeil |
| 8,167,869 B2 | 5/2012 | Wudyka |
| 8,207,392 B2 | 6/2012 | Haggstrom et al. |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,444,612 B2 | 5/2013 | Patel et al. |
| 8,449,508 B2 | 5/2013 | Coulthard et al. |
| 8,500,776 B2 | 8/2013 | Ebner |
| 8,529,548 B2 | 9/2013 | Blott et al. |
| 8,545,464 B2 | 10/2013 | Weston |
| 8,545,466 B2 | 10/2013 | Andresen et al. |
| 8,569,566 B2 | 10/2013 | Blott et al. |
| 8,603,074 B2 | 12/2013 | Kagan |
| 8,604,265 B2 | 12/2013 | Locke et al. |
| 8,628,505 B2 | 1/2014 | Weston |
| 8,641,691 B2 | 2/2014 | Fink |
| 8,641,693 B2 | 2/2014 | Locke et al. |
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,829,263 B2 | 9/2014 | Haggstrom et al. |
| 8,870,837 B2 | 10/2014 | Locke et al. |
| 8,915,895 B2 | 12/2014 | Jaeb et al. |
| 8,961,496 B2 | 2/2015 | Locke et al. |
| 8,974,429 B2 | 3/2015 | Gordon et al. |
| 9,050,209 B2 | 6/2015 | Coulthard et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,168,330 B2 | 10/2015 | Joshi et al. |
| 9,198,802 B2 | 12/2015 | Robinson et al. |
| 9,220,822 B2 | 12/2015 | Hartwell et al. |
| 9,259,558 B2 | 2/2016 | Tsai |
| 9,265,665 B2 | 2/2016 | Robinson et al. |
| 9,265,867 B2 | 2/2016 | Coulthard et al. |
| 9,283,118 B2 | 3/2016 | Locke et al. |
| 9,414,968 B2 | 8/2016 | Heagle |
| 9,421,133 B2 | 8/2016 | Hu et al. |
| 9,427,505 B2 | 8/2016 | Askem et al. |
| 9,452,088 B2 | 9/2016 | Shulman et al. |
| 9,560,975 B2 | 2/2017 | Mei et al. |
| 9,629,986 B2 | 4/2017 | Patel et al. |
| D787,690 S | 5/2017 | Mackay et al. |
| 9,669,138 B2 | 6/2017 | Joshi et al. |
| 9,737,649 B2 | 8/2017 | Begin et al. |
| 9,814,811 B2 | 11/2017 | Aalders et al. |
| 9,925,092 B2 | 3/2018 | Luckemeyer et al. |
| RE46,778 E | 4/2018 | Peron |

(56) References Cited

U.S. PATENT DOCUMENTS

| | | |
|---|---|---|
| 9,956,120 B2 | 5/2018 | Locke |
| 10,004,914 B2 | 6/2018 | Nettesheim et al. |
| 10,010,656 B2 | 7/2018 | Jaeb et al. |
| 10,016,544 B2 | 7/2018 | Coulthard et al. |
| 2001/0034499 A1 | 10/2001 | Sessions et al. |
| 2003/0212357 A1 | 11/2003 | Pace |
| 2004/0064132 A1 | 4/2004 | Boehringer et al. |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0259102 A1 | 11/2006 | Slatkine |
| 2007/0055209 A1 | 3/2007 | Patel et al. |
| 2007/0066946 A1* | 3/2007 | Haggstrom ......... A61M 1/0088 604/313 |
| 2007/0078366 A1* | 4/2007 | Haggstrom ......... A61M 1/0031 602/53 |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2007/0265586 A1 | 11/2007 | Joshi et al. |
| 2008/0021356 A1 | 1/2008 | Castello Escude et al. |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2011/0092927 A1 | 4/2011 | Wilkes et al. |
| 2011/0112492 A1 | 5/2011 | Bharti et al. |
| 2011/0178451 A1 | 7/2011 | Robinson et al. |
| 2011/0224631 A1 | 9/2011 | Simmons |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2012/0109083 A1 | 5/2012 | Coulthard et al. |
| 2013/0090615 A1 | 4/2013 | Jaeb et al. |
| 2013/0102979 A1 | 4/2013 | Coulthard et al. |
| 2013/0165821 A1* | 6/2013 | Freedman ............ A61M 1/0084 601/2 |
| 2013/0215638 A1 | 8/2013 | Dabov et al. |
| 2014/0005618 A1 | 1/2014 | Locke et al. |
| 2014/0100536 A1 | 4/2014 | Angel |
| 2014/0343518 A1 | 11/2014 | Riesinger |
| 2015/0057625 A1 | 2/2015 | Coulthard et al. |
| 2015/0065965 A1 | 3/2015 | Haggstrom et al. |
| 2015/0073358 A1 | 3/2015 | Jaeb et al. |
| 2015/0174304 A1* | 6/2015 | Askem ................ A61M 1/0027 604/319 |
| 2015/0202354 A1 | 7/2015 | Wall |
| 2015/0224238 A1 | 8/2015 | Hartwell |
| 2015/0250931 A1 | 10/2015 | Bharti et al. |
| 2016/0015873 A1 | 1/2016 | Robinson et al. |
| 2016/0081859 A1 | 3/2016 | Hartwell |
| 2016/0166438 A1 | 6/2016 | Rovaniemi |
| 2016/0199546 A1 | 7/2016 | Chao |
| 2016/0242964 A1 | 8/2016 | Rapp et al. |
| 2016/0270967 A1 | 9/2016 | Hartwell |
| 2016/0271305 A1 | 9/2016 | Kurihara et al. |
| 2016/0361473 A1 | 12/2016 | Robinson et al. |
| 2017/0095598 A1 | 4/2017 | Joshi et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0319761 A1 | 11/2017 | Locke et al. |
| 2017/0368239 A1 | 12/2017 | Askem et al. |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0200414 A1 | 7/2018 | Askem et al. |
| 2018/0272052 A1 | 9/2018 | Locke et al. |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0021911 A1 | 1/2019 | Askem et al. |
| 2019/0159938 A1 | 5/2019 | Askem et al. |

FOREIGN PATENT DOCUMENTS

| | | |
|---|---|---|
| EP | 0512543 A2 | 11/1992 |
| EP | 1411874 A1 | 4/2004 |
| EP | 1455701 B1 | 3/2006 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2326295 A1 | 6/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 2659915 A1 | 11/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2 345 437 | 4/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2829287 A1 | 1/2015 |
| EP | 2683285 B1 | 2/2015 |
| EP | 2470136 B1 | 3/2015 |

(56) References Cited

FOREIGN PATENT DOCUMENTS

| | | | |
|---|---|---|---|
| EP | 2503974 | B1 | 5/2015 |
| EP | 2249894 | B1 | 8/2015 |
| EP | 2802366 | B1 | 8/2015 |
| EP | 2438302 | B1 | 9/2015 |
| EP | 2346545 | B1 | 10/2015 |
| EP | 2438301 | B1 | 10/2015 |
| EP | 2802304 | B1 | 12/2015 |
| EP | 2852421 | B1 | 1/2016 |
| EP | 2410962 | B1 | 3/2016 |
| EP | 2640436 | B1 | 3/2016 |
| EP | 2855937 | B1 | 5/2016 |
| EP | 2433594 | B1 | 6/2016 |
| EP | 2919730 | B1 | 6/2016 |
| EP | 2861869 | B1 | 7/2016 |
| EP | 2945584 | B1 | 7/2016 |
| EP | 2293749 | B1 | 8/2016 |
| EP | 3072542 | A2 | 9/2016 |
| EP | 2305327 | B1 | 10/2016 |
| EP | 2467086 | B1 | 10/2016 |
| EP | 2470135 | B1 | 10/2016 |
| EP | 2767305 | B1 | 10/2016 |
| EP | 2282788 | B1 | 12/2016 |
| EP | 2462956 | B2 | 3/2017 |
| EP | 3139878 | A1 | 3/2017 |
| EP | 2249761 | B1 | 4/2017 |
| EP | 1587502 | B1 | 5/2017 |
| EP | 1587554 | B1 | 5/2017 |
| EP | 2731563 | B1 | 5/2017 |
| EP | 2968871 | B1 | 7/2017 |
| EP | 2632613 | B1 | 8/2017 |
| EP | 2781208 | B1 | 8/2017 |
| EP | 2888478 | B1 | 8/2017 |
| EP | 2937107 | B1 | 8/2017 |
| EP | 2967627 | B1 | 8/2017 |
| EP | 3062751 | B1 | 8/2017 |
| EP | 3139879 | B1 | 8/2017 |
| EP | 2359784 | B1 | 9/2017 |
| EP | 3151795 | B1 | 9/2017 |
| EP | 2367518 | B1 | 10/2017 |
| EP | 2675493 | B1 | 10/2017 |
| EP | 3068455 | B1 | 10/2017 |
| EP | 2558046 | B2 | 11/2017 |
| EP | 2736548 | B1 | 11/2017 |
| EP | 3052158 | B1 | 11/2017 |
| EP | 2825220 | B1 | 12/2017 |
| EP | 2593058 | B1 | 3/2018 |
| EP | 3139880 | B1 | 3/2018 |
| EP | 1496822 | B1 | 8/2018 |
| EP | 2879633 | B1 | 8/2018 |
| EP | 2227203 | B1 | 9/2018 |
| EP | 2696826 | B1 | 9/2018 |
| EP | 3106186 | B1 | 9/2018 |
| EP | 3162330 | B1 | 9/2018 |
| EP | 3169382 | B1 | 9/2018 |
| EP | 3203953 | B1 | 9/2018 |
| EP | 2941280 | B1 | 10/2018 |
| EP | 3244852 | B1 | 10/2018 |
| EP | 2687241 | B2 | 11/2018 |
| EP | 2687243 | B2 | 11/2018 |
| EP | 3062753 | B1 | 11/2018 |
| EP | 3120879 | B1 | 12/2018 |
| EP | 3191149 | B1 | 1/2019 |
| EP | 2370130 | B1 | 3/2019 |
| EP | 3053609 | B1 | 3/2019 |
| EP | 3180048 | B1 | 3/2019 |
| EP | 3143974 | B1 | 4/2019 |
| EP | 2285432 | B2 | 6/2019 |
| EP | 3050545 | B1 | 7/2019 |
| EP | 3319656 | B1 | 8/2019 |
| EP | 2355762 | B1 | 9/2019 |
| EP | 2822613 | B1 | 9/2019 |
| EP | 2863855 | B1 | 9/2019 |
| EP | 2482912 | B1 | 10/2019 |
| EP | 3038667 | B1 | 10/2019 |
| EP | 3129095 | B1 | 10/2019 |
| EP | 3191150 | B1 | 10/2019 |
| EP | 3280466 | B1 | 10/2019 |
| EP | 2244756 | B1 | 12/2019 |
| EP | 2968702 | B1 | 12/2019 |
| FR | 2939320 | A1 | 6/2010 |
| GB | 2511523 | A | 9/2014 |
| JP | H04-354722 | A | 12/1992 |
| JP | 2014-210023 | A | 11/2014 |
| RU | 131622 | U1 | 8/2013 |
| WO | WO 1996/05873 | | 2/1996 |
| WO | WO-2006114637 | A2 | 11/2006 |
| WO | WO 2007/030601 | A2 | 3/2007 |
| WO | WO 2009/098696 | A2 | 8/2009 |
| WO | WO-2009111657 | A2 | 9/2009 |
| WO | WO 2009/120951 | A2 | 10/2009 |
| WO | WO 2011/130570 | A1 | 10/2011 |
| WO | WO 2011/135285 | A1 | 11/2011 |
| WO | WO 2013/136181 | | 9/2013 |
| WO | WO 2013/175306 | | 11/2013 |
| WO | WO 2014/099709 | | 6/2014 |
| WO | WO 2016/126560 | A1 | 8/2016 |
| WO | WO 2016/174048 | | 11/2016 |
| WO | WO 2017/079174 | A1 | 5/2017 |

OTHER PUBLICATIONS

International Preliminary Report on Patentability for Application No. PCT/EP2016/059329, dated Nov. 9, 2017, 7 pages.
Communication of a Notice of Opposition, first information to patent proprietor—Statement of Facts and Arguments for the European Patent No. 3288508, dated Oct. 12, 2020, 26 pages.
Communication of further notices of opposition pursuant to Rule 79(2) EPC for European Patent No. 3288508, dated Oct. 20, 2020, 2 pages.

* cited by examiner

REDUCED PRESSURE APPARATUSES AND METHODS

CROSS-REFERENCE TO RELATED APPLICATIONS

This application is a U.S. national stage application of International Patent Application No. PCT/EP2016/059329, filed on Apr. 26, 2016, which claims the benefit of U.S. Provisional Application No. 62/153,483, filed Apr. 27, 2015, and U.S. Provisional Application No. 62/154,078, filed Apr. 28, 2015, the entireties of both of which are hereby incorporated by reference.

BACKGROUND

Field

Embodiments described herein relate to apparatuses, systems, and methods the treatment of wounds, for example using dressings in combination with negative pressure wound therapy.

Background

Prior art dressings for use in negative pressure have included a negative pressure source located in a remote location form the wound dressing. Having a remote negative pressure source such as a pump can be inconvenient to a user, who must find a place to locate the negative pressure source and must deal with the inconvenience of having tubing or other components connecting the negative pressure source with the wound dressing. Attempts have been made to incorporate a negative pressure source into the wound dressing. In these wound dressings, moisture from the wound can make it difficult to incorporate electronic components into the dressing.

Prior art dressings for use in negative pressure can also be difficult to apply, particularly around curved or non-flat body surfaces. When additional components are added to the wound dressing, this can make the wound dressing even more difficult to apply and uncomfortable to the user. Dressings which absorb and retain wound exudate can also be aesthetically unpleasing if the wound exudate is visible, making the wound dressing difficult to address in social situations.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein. In some embodiments, a negative pressure source is incorporated into a wound dressing apparatus so that the wound dressing and the negative pressure source are part of an integral or integrated wound dressing structure that is applied simultaneously to a patient's wound.

In some aspects, a wound dressing apparatus comprises a wound contact layer configured to be positioned in contact with a wound, a first cover layer positioned over the wound contact layer, one or more spacer layers positioned between the wound contact layer and the first cover layer, wherein a spacer layer is positioned on an upper surface of the wound contact layer, an absorbent layer positioned over the spacer layer positioned on the upper surface of the wound contact layer, a negative pressure source configured to be in fluid communication with the wound, the negative pressure source configured to draw wound fluid through the one or more spacer layers into the absorbent layer, wherein the negative pressure source is located in one or both of a recess of a spacer layer or the absorbent layer, and a pocket or chamber defined at least in part by the first cover layer, and a first filter provided in a flow path between the negative pressure source and the wound contact layer.

The apparatus of the preceding paragraph may also include any combination of the following features described in this paragraph, among others described herein. The negative pressure source may be located in a recess in the absorbent layer. The absorbent layer may be positioned between the wound contact layer and the first cover layer. The first filter may be located in the first cover layer. The negative pressure source can be located in a chamber defined between the first cover layer and a second cover layer placed over the first cover layer. The apparatus can include a spacer layer or absorbent layer between the first cover layer and the second cover layer. A second filter can be located in the second cover layer. The apparatus can include a third cover layer positioned over the second cover layer, the third cover layer defining a chamber between the second cover layer and the third cover layer. The apparatus can include a further absorbent and/or spacer layer within the chamber defined between the second cover layer and the third cover layer. The apparatus can include a third filter in the third cover layer. The first cover layer can be positioned on an upper surface of the absorbent layer. The first cover layer can be sealed to the wound contact layer. The apparatus can include one or more ultrasonic oscillators. The one or more spacer layers can comprise a recess or pouch for receiving the absorbent layer and/or the negative pressure source. The negative pressure source can be positioned beneath the absorbent layer. The apparatus can include a pressure fuse configured to discontinue operation of the negative pressure source if the pressure exceeds a threshold pressure. The apparatus can include channels around a perimeter of the absorbent layer and across a middle of the absorbent layer to expose portions an underlying spacer layer. The apparatus can include a tube filled with magnetic fluid for creating negative pressure in the apparatus. The electronic components associated with the negative pressure source can be positioned in separate recesses within the absorbent layer and/or spacer layers.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which.

DETAILED DESCRIPTION

Figure 1:
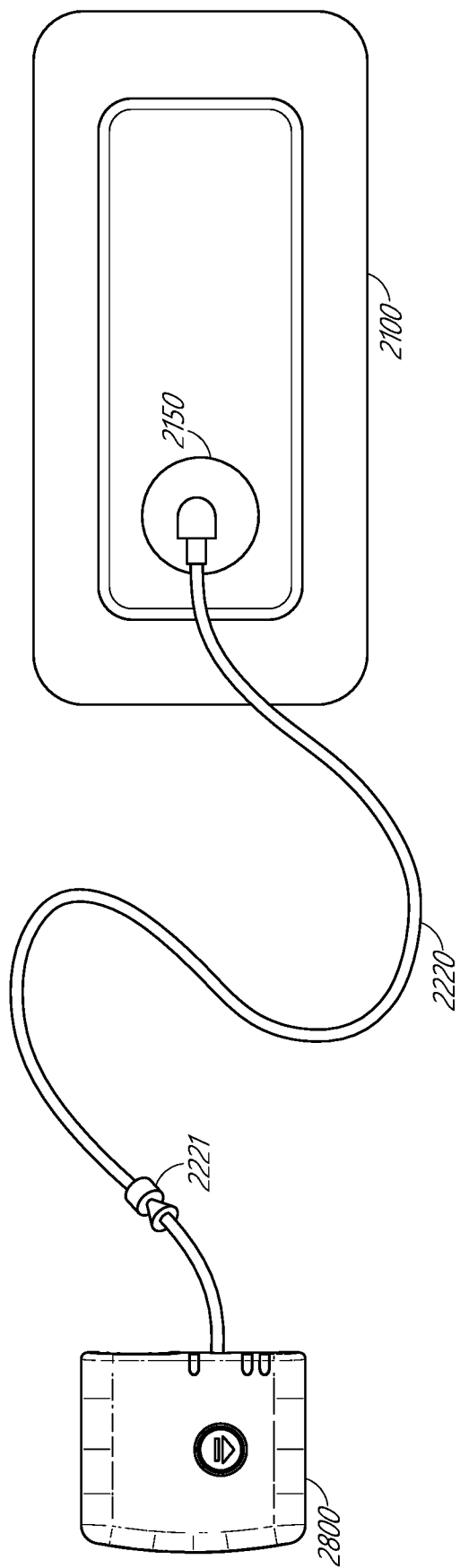
FIG. 1 illustrates an embodiment of a topical negative pressure wound treatment apparatus comprising a wound dressing in combination with a pump.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated and considered to be part of this specification, that is directed to embodiments, methods of manufacture, and wound dressing components and wound treatment apparatuses that may be used in combination or in addition to the embodiments described herein. Additionally, embodiments of the wound dressings, wound treatment apparatuses and methods described herein may also be used in combination or in addition to those described in U.S. Provisional Application No. 61/650,904, filed May 23, 2012, titled "APPARATUSES AND METHODS FOR NEGATIVE PRESSURE WOUND THERAPY," International Application No. PCT/IB2013/001469, filed May 22, 2013, titled "APPARA- TUSES AND METHODS FOR NEGATIVE PRESSURE WOUND THERAPY," and published as WO 2013/175306 on Nov. 28, 2013, U.S. Provisional Application No. 61/678, 569, filed Aug. 1, 2012, titled "WOUND DRESSING AND METHOD OF TREATMENT," U.S. Provisional Application No. 61/753,374, filed Jan. 16, 2013, titled "WOUND DRESSING AND METHOD OF TREATMENT," U.S. Provisional Application Ser. No. 61/753,878, filed Jan. 17, 2013, titled "WOUND DRESSING AND METHOD OF TREATMENT," U.S. Provisional Application No. 61/785, 054, filed Mar. 14, 2013, titled "WOUND DRESSING AND METHOD OF TREATMENT," U.S. Provisional Application No. 61/823,298, filed May 14, 2013, titled "WOUND DRESSING AND METHOD OF TREATMENT," International Application No. PCT/IB2013/002102, filed Jul. 31, 2013, titled "WOUND DRESSING AND METHOD OF TREATMENT," and published as WO 2014/020443 on Feb. 6, 2014, and International Application No. PCT/IB2013/002060, filed Jul. 31, 2013, titled "WOUND DRESSING," and published as WO 2014/020440 on Feb. 6, 2014, the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21 2011, published as US2011/0282309, titled "WOUND DRESSING AND METHOD OF USE," and which is hereby incorporated by reference in its entirety, including further details relating to embodiments of wound dressings, the wound dressing components and principles, and the materials used for the wound dressings.

FIG. 1 illustrates an embodiment of a TNP wound treatment comprising a wound dressing 2100 in combination with a pump 2800. As stated above, the wound dressing 2100 can be any wound dressing embodiment disclosed herein including without limitation dressing embodiment 100 or have any combination of features of any number of wound dressing embodiments disclosed herein. Here, the dressing 2100 may be placed over a wound, and a conduit 2220 may then be connected to the port 2150, although in some embodiments the dressing 2100 may be provided with at least a portion of the conduit 2220 preattached to the port 2150. Preferably, the dressing 2100 is provided as a single article with all wound dressing elements (including the port 2150) pre-attached and integrated into a single unit. The wound dressing 2100 may then be connected, via the conduit 2220, to a source of negative pressure such as the pump 2800. The pump 2800 can be miniaturized and portable, although larger conventional pumps may also be used with the dressing 2100. In some embodiments, the pump 2800 may be attached or mounted onto or adjacent the dressing 2100. A connector 2221 may also be provided so as to permit the conduit 2220 leading to the wound dressing 2100 to be disconnected from the pump, which may be useful for example during dressing changes.

Figure 2:
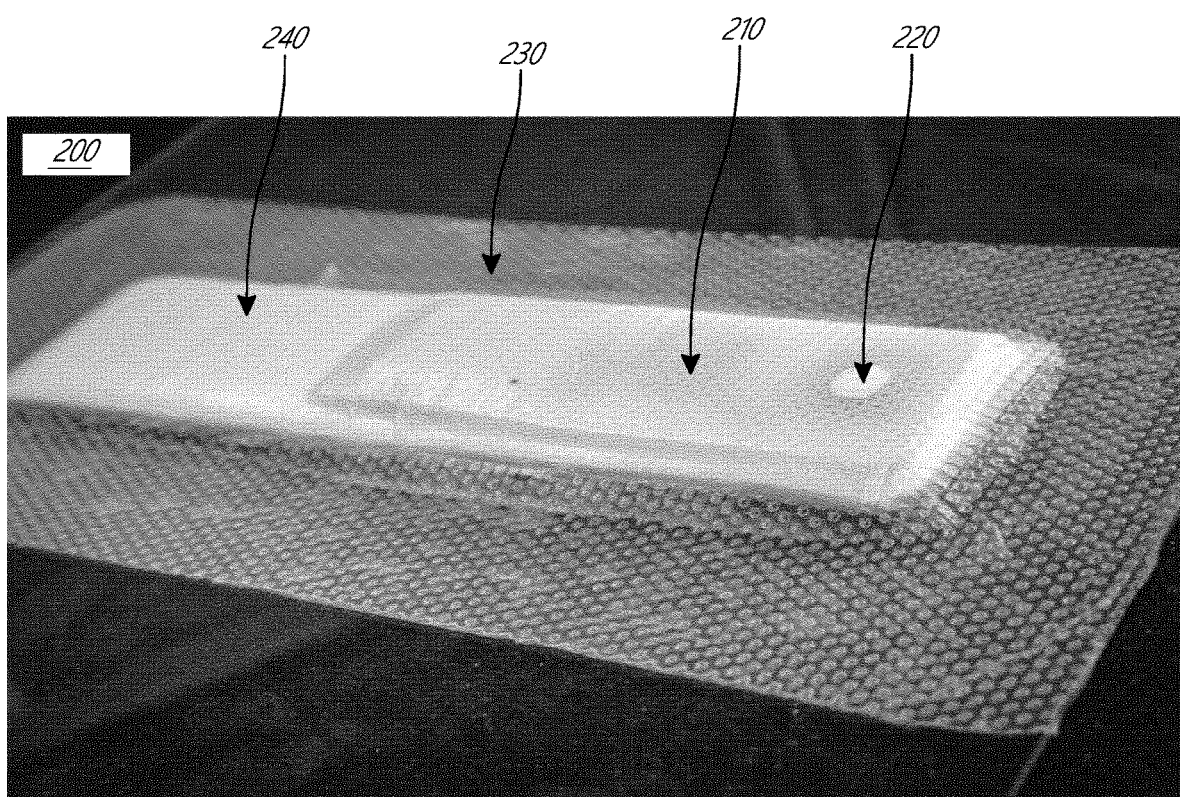
FIG. 2 illustrates an embodiment of a source of negative pressure and battery integrated on top of a dressing layer.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. As is illustrated in FIG. 2, the source of negative pressure and battery can be included within the integrated dressing 200. Although FIG. 2 illustrates the source of negative pressure and battery 210 placed on top of the dressing layer 240 (such as an absorbent layer), the source of negative pressure and one or more components can be incorporated into the dressing differently. The source of negative pressure and the one or more components need not all be incorporated into the dressing in the same manner. For example, a pressure sensor can be positioned below (or closer to the wound) the layer 240 while the source of negative pressure can be positioned on top of the layer 240. FIGS. 6A-6D illustrate alternative arrangements for incorporating the negative pressure source and the one or more components into the dressing. The integrated dressing 200 illustrated in FIG. 2 includes a cover layer 230 for securing the dressing to skin surrounding the wound. The cover layer 230 can be formed of substantially fluid impermeable material, such as a film. The cover layer can include an adhesive for securing the dressing to the surrounding skin or to a wound contact layer, described further below.

In some embodiments, the dressing can include the power source and other components, such as electronics, on and/or incorporated into the dressing and can utilize a wound contact layer and a first spacer layer within the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound. The first spacer layer assists in distributing negative pressure over the wound site and facilitating transport of wound exudate and fluids into the wound dressing. Further, an absorbent layer (such as layer 240) for absorbing and retaining exudate aspirated from the wound can be utilized. In some embodiments, the absorbent layer includes a shaped form of a superabsorber layer with recesses or compartments for the pump, electronics, and accompanying components. These layers can be covered with one layer of a film or cover layer (or a first cover layer). The first cover layer can include a filter set (such as a filter provided at an opening in the first cover layer) that can be positioned within or over one of the recesses. The filter can be configured to align with one of the at least one recesses of the absorbent layer, and the filter can include hydrophobic material to protect the pump and/or other components from liquid exudates. The filter can block fluids while permitting gases to pass through. The pump, electronics, switch and battery can be positioned on top of the first cover layer. Another section of spacer, a second spacer, can be positioned above and/or surrounding the pump. In some embodiments, the second spacer can be smaller than the first spacer used above the wound contact layer. A section of top film or cover layer (or a second cover layer) is positioned over the top of the second spacer with a second filter associated with or positioned within the second cover layer (such as at an opening in the second cover layer). In some embodiments, the first and second cover layer can be made of the same material. In some embodiments, the first and second cover layers can be made of different material.

A second filter can be alternative or additionally used. For example, the second filter 220 can be constructed from antibacterial and/or antimicrobial materials so that the pump can exhaust gases into the atmosphere. Filter 220 can also help to reduce noise produced by the pump.

In certain embodiments, the first and second cover layers include a moisture vapor permeable material that protects the pump and electronic components from liquid exudate removed from the wound and other liquids, while allowing gases through. The pump and electronics can be pouched between the fluid impermeable membranes or cover layers with the only input and output being a filter on each side of the pump. The membranes and filter can protect the electronics from liquid from both sides. In some embodiments, the dressing and integrated electronics pouch can be used in the shower and/or can be in contact with liquid without impeding the operation of the pump and dressing.

In some embodiments, in addition to or instead of one or more batteries, one or more alternative energy generators (such as RF energy harvester, thermal energy harvester, and the like) can be included into the pump to provide an alternative to traditional power sources. Examples of energy harvesters are described in U.S. Provisional Application No. 62/097,273, filed on Dec. 29, 2014, and titled "Negative Pressure Wound Therapy Apparatus and Methods for Operating the Apparatus," U.S. Provisional Application No. 62/172,704, filed on Jun. 8, 2015, and titled "Negative Pressure Wound Therapy Apparatus and Methods for Operating the Apparatus," and International Application PCT/EP2015/080740, titled "Negative Pressure Wound Therapy Apparatus and Method of Operating the Apparatus" and filed on Dec. 21, 2015 the disclosures of which are incorporated in their entirety.

Figure 3:
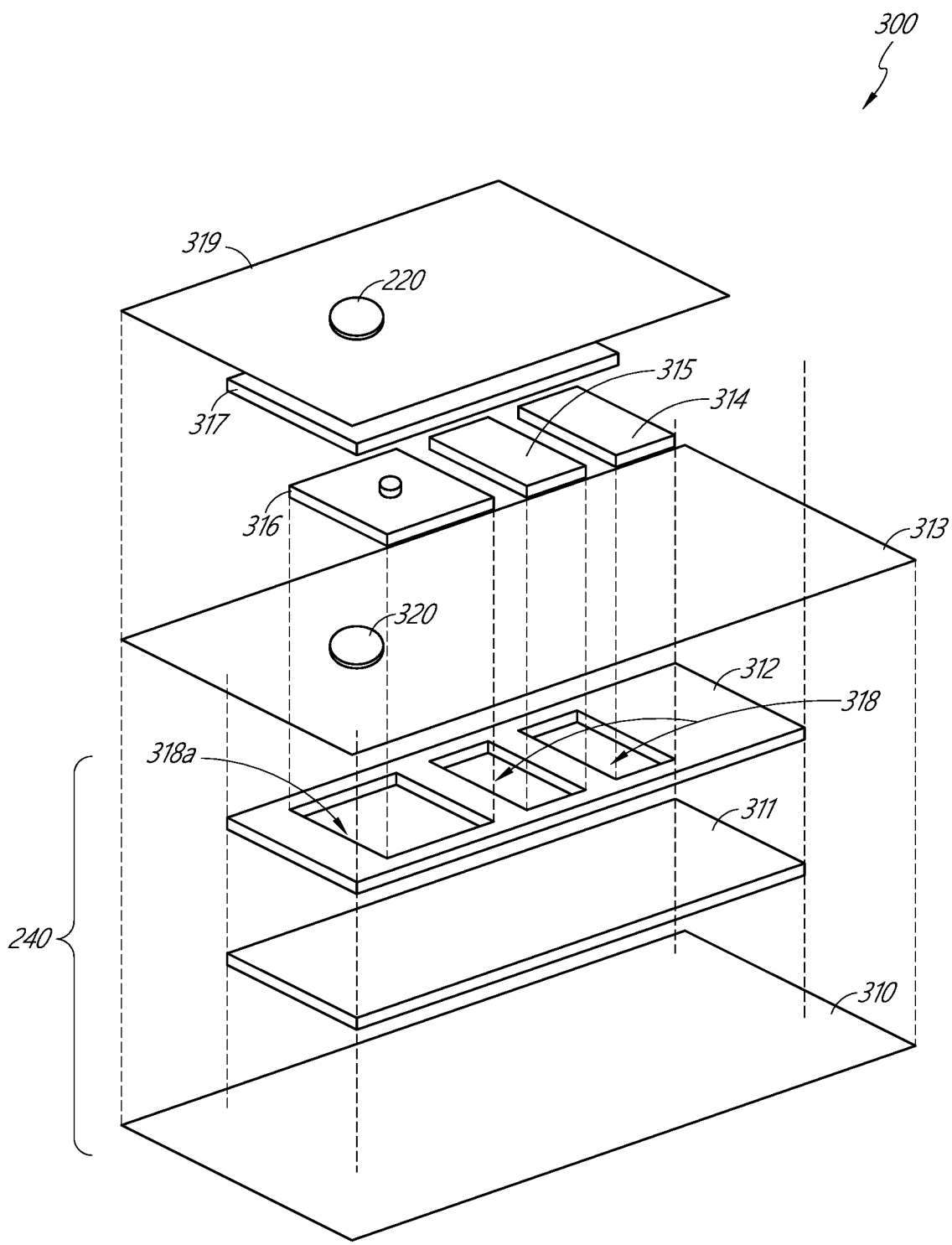
FIG. 3 illustrates an embodiment of layers of a wound dressing with integrated pump and electronic components.

FIG. 3 illustrates the layers of a wound dressing 300 with integrated pump and electronic components, such as a controller configured to control the pump, according to some embodiments. The dressing layer 240 includes a wound contact layer 310, a spacer layer 311, and an absorbent layer 312. In some embodiments, the spacer layer 311 can be formed at least partially from a three dimensional (3D) fabric. In certain embodiments, a superabsorbent material can be used in the absorbent layer 312. The absorbent layer 312 can include one or more recesses 318 (and 318a) within the layer to accommodate placement of the pump, electronics, and/or power source. A moisture vapor permeable top film or first cover layer 313 is positioned above the absorbent layer 312. The cover layer 313 can include a filter 320. The filter can be positioned in line with and above a recess 318a in the absorbent layer 212.

A pump 316, electronics package 315, and power source 314 (such as a battery) can be positioned above the cover layer 313 as shown in FIG. 3. The pump 316, electronics package 315, and power source 314 can be positioned on top of the cover layer 313 and at least partially depressed into the corresponding recesses 318 (and 318a) in the absorbent layer 312. For example, the pump 316 can be at least partially depressed in the recess 318a. A packing layer 317 can be positioned above and/or surrounding the pump 316, electronics package 315, and power source 314. The packing layer 317 can be formed from spacer material and/or absorbent material. The packing layer 317 can include 3D spacer. In some embodiments, the packing layer 317 additionally or alternatively can include a superabsorbent material. A second moisture vapor permeable top film or second cover layer 319 can be positioned over and seal the packing layer 317, pump 316, electronics package 315, and power source 314. The second cover layer 319 can also include a second filter 220.

In some embodiments, the operation of the pump can vary depending on the environmental humidity level. It can be advantageous to provide mechanisms to drive moisture out of the dressing or otherwise limit or control the humidity of the dressing. In some embodiments, a chamber generated by the layers above the pump can be used to act as a pressurized sink for gases (such as gases exhausted by the pump), thereby increasing the relative humidity (or RH) and delta RH across the outer membrane, which in turn can increase the rate of evaporation.

Figure 4:
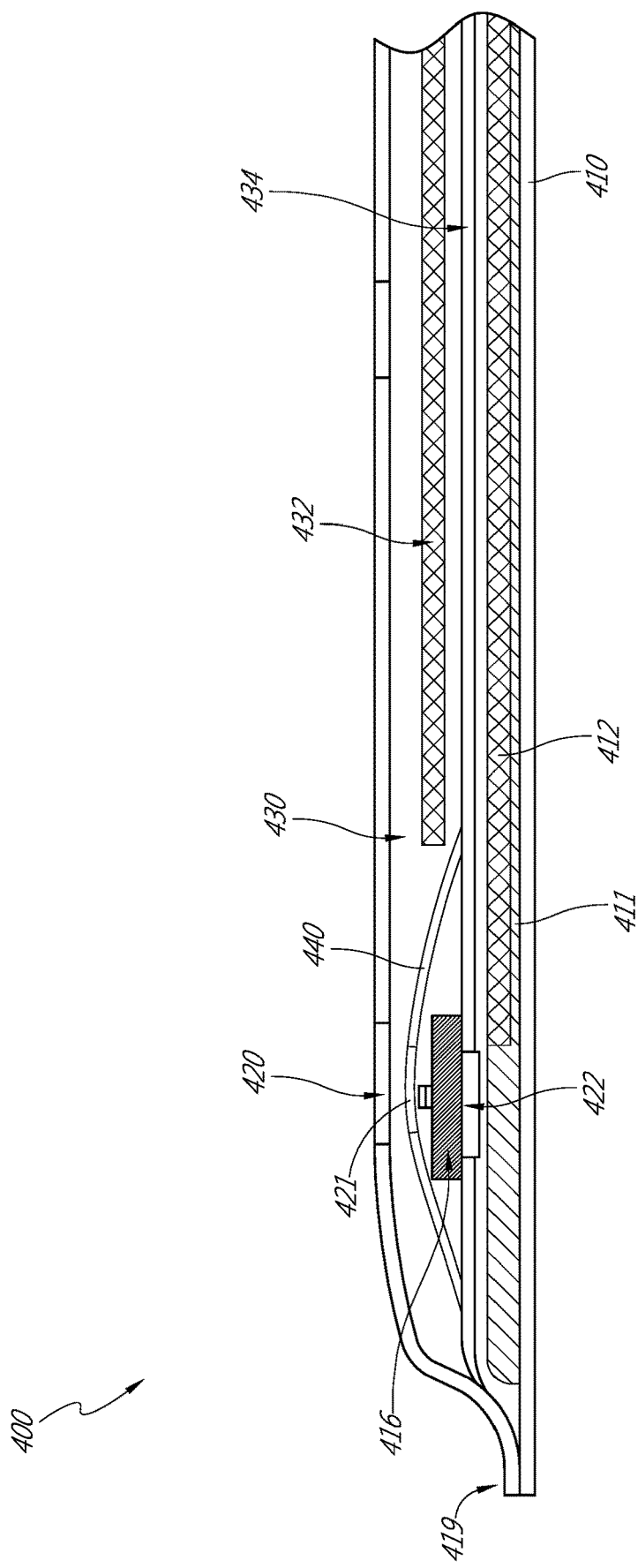
FIG. 4 illustrates an embodiment of a cross-section of an integrated wound dressing.

FIG. 4 illustrates a cross-section of an integrated wound dressing 400 showing the various layers according to some embodiments. The dressing includes a wound contact layer 410, a spacer layer 411, and an absorbent layer 412, and a first cover layer 434. The first cover layer 434 is positioned to cover and form a seal over the absorbent layer 412, spacer layer 411, and wound contact layer 410. The dressing 400 can include three filters 420, 421, 422. First filter 422 can be provided in the first cover layer 434 below the pump and electronic components similar to the first filter 320 in the first cover layer 313 as described with reference to FIG. 3. The dressing 400 can include a second filter 421 positioned above a pump 416 as is shown in FIG. 4. The second filter 421 may be configured to be in fluid communication with the exhaust of the pump 416. In some embodiments, the second filter 421 can be integrated into an optional layer 440 (which may be considered another cover layer, and may be a moisture vapor permeable film) of material that encloses the pump between the first cover layer and the optional layer as shown in FIG. 4. In operation, the pump 416 inflates chamber 430 with gases removed from the wound. After inflation, chamber 430 can provide both bolstering and cushioning of the dressing 400. As shown in FIG. 4, an optional superabsorber 432 can be included in the chamber 430 above layer 434 and below the moisture vapor permeable top film or second cover layer 419. In such embodiments, the superabsorber 432 can draw fluid through the cover layer 434, and the increased pressure in chamber 430 can facilitate an increased evaporation to atmosphere. A third filter 420 can be positioned within or adjacent to the second moisture vapor permeable top film or second cover layer 419 (such as at an opening in the cover layer 419). Filter 420 can function similar to filter 220 illustrated in FIG. 2. In some embodiments, the third filter 420 can be alternative or additionally used to exhaust gas from the dressing to the atmosphere. For example, the third filter 420 can be constructed from antibacterial and/or antimicrobial materials so that the pump and/or dressing chamber created by the multiple cover layers can exhaust gases into the atmosphere.

In some embodiments, the pump can include a piezoelectric transducer that causes negative pressure to be supplied to the wound. In certain embodiments, a secondary device (such as a secondary piezoelectric device) can be used to generate atomisation of the fluid in the dressing, either accelerating evaporation of the water portion of the wound fluid or firing it through the moisture vapor permeable (MVP) top film where it can then evaporate. This can reduce or eliminate the effect of environmental humidity on the capability of the dressing to evaporate water.

Figure 5:
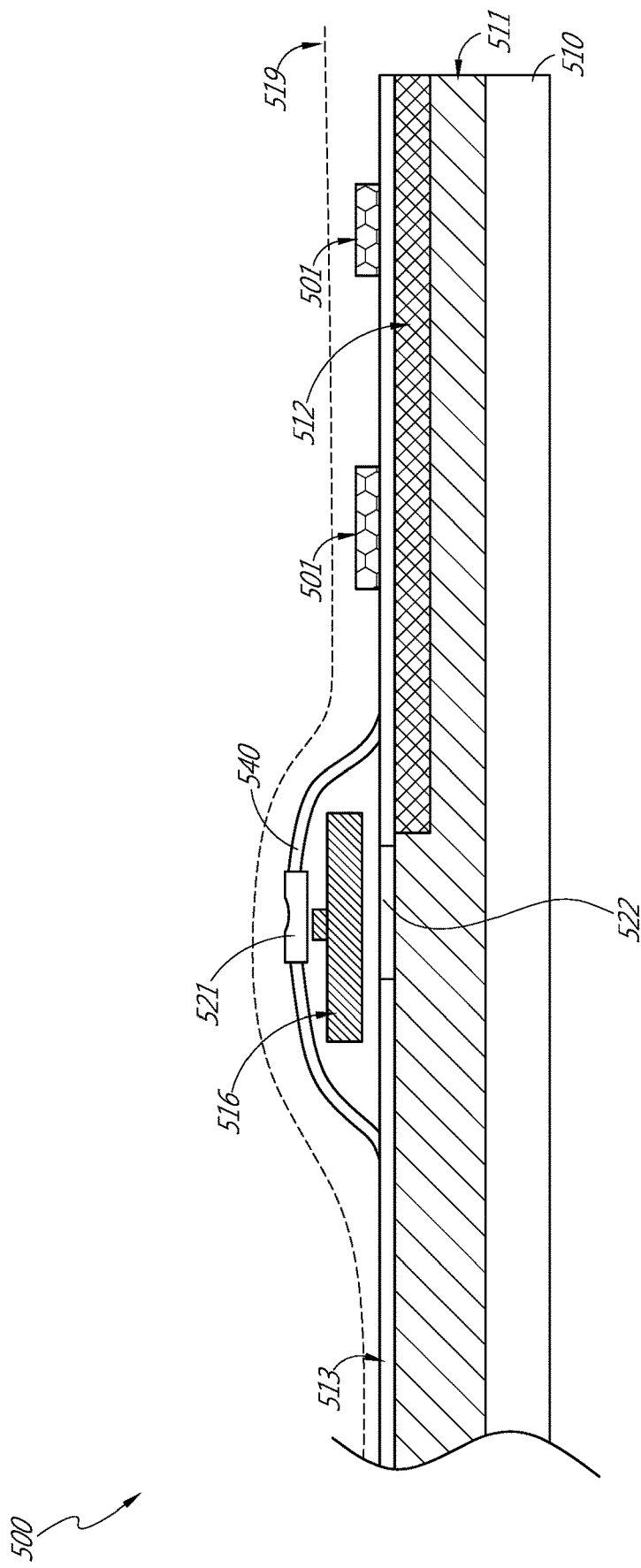
FIG. 5 illustrates an embodiment of a cross-section of an integrated wound dressing with ultrasonic oscillation.

FIG. 5 illustrates a cross-section of an integrated wound dressing 500 according to some embodiments. In the illustrated dressing 500, a top layer or second cover layer 519 is optional. The dressing 500 includes a wound contact layer 510, a spacer layer 511, and an absorbent layer/superabsorber 512 below a top film or first cover layer 513. In some embodiments, one or more ultrasonic oscillators 501 which may be positioned on the first cover layer 513 can be used to atomize water from the superabsorber and/or absorbent layer 512 or from the space between the top film or first cover layer 513 and the optional top film or second cover layer 519. The first cover layer 513 can include a first filter 522 in communication with an inlet of a negative pressure pump 516 positioned over the first cover layer 513, and the optional second cover layer 519 can include a second filter 521 in communication with a pump exhaust of pump 516. In some embodiments, the second filter 521 can be integrated into an optional layer 540 of material that encloses the pump between the first cover layer and the optional layer 540 as shown in FIG. 5. In some embodiments, oscillation can be provided by the pump 516. In such embodiments, the one or more ultrasonic oscillators 501 would not be included in the dressing because the pump 516 is providing the oscillation.

In some embodiments, as described below, the pump, electronics and/or associated components can be contained in single or multiple sealed pockets or pouches. The pockets or pouches can include the pump, electronics, and/or power source(s) (such as batteries) with or without a spacer layer and/or absorbent layer padding. The packets may be designed to allow easy separation of the electronics from the dressing for disposal.

Figure 6A:
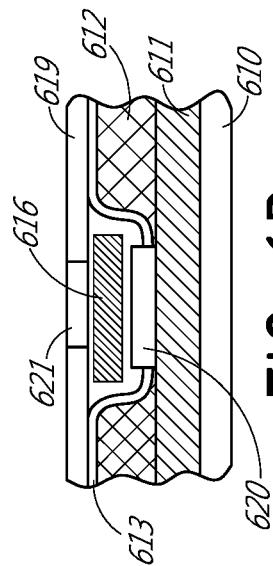
FIGS. 6A-6D illustrates embodiments of a pump pouch or pockets according to some embodiments.
Figure 6B:
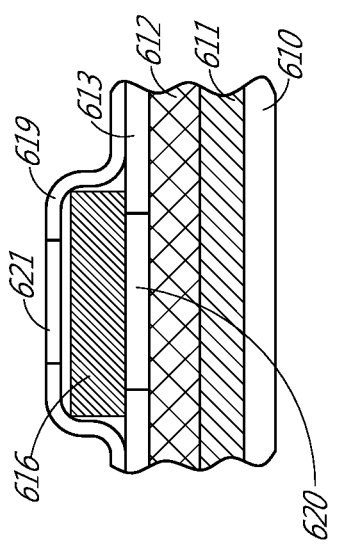

FIGS. 6A-6D illustrate embodiments of a pump pouch or pockets according to some embodiments. FIG. 6A illustrates an integrated wound dressing similar to the dressing described with reference to FIG. 2-4 in which a pump 616 is placed between the first cover layer 613 and the second cover layer 619. The dressing includes, from the bottom up, a wound contact layer 610, a spacer layer 611, an absorbent layer or superabsorber 612, and one or more moisture vapor permeable cover layers. The dressing as shown in FIG. 6A, does not include a spacer layer or absorbent layer between the first cover layer 613 and second cover layer 619. Additionally, the pump 616 is positioned above the first cover layer 613 placed above the absorbent layer 612 and no recess is formed in the absorbent layer 612 for the pump. The electronics and power source(s) can be similarly placed. FIG. 6B illustrates an integrated wound dressing in which a pump 616 is positioned above the first cover layer 613 in a recess of the absorbent layer 612. The dressing includes, from the bottom up, a wound contact layer 610, a spacer layer 611, an absorbent layer or superabsorber 612, and one or more cover layers which may be moisture vapor permeable. The positioning of the pump 616 above the first cover layer 613 in a recess of the absorbent layer 612 is similar to that illustrated in FIG. 3 but the embodiment shown in FIG. 6B does not include a spacer layer or absorbent layer between the first cover layer and second cover layer. Electronics and power source(s) can be similarly placed.

Figure 6C:
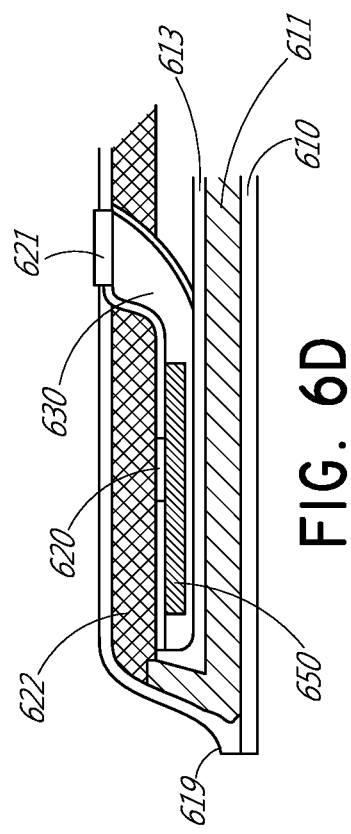
Figure 6D:
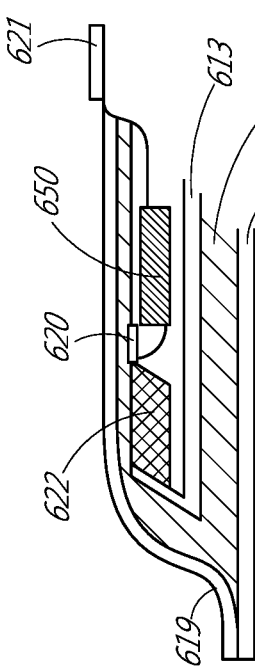

FIGS. 6C-6D illustrate embodiments of wound dressings comprising a pump and electronics package 650. The package 650 can also include power source(s). The dressing includes a wound contact layer 610, a spacer layer 611, an absorbent layer or superabsorber 612, and one or more cover layers which may be moisture vapor permeable. The pump and electronics package 650 can be positioned in the dressing as described with reference to FIG. 3. In other embodiments, the pump and electronics packages 650 can be positioned in alternative positions than what is described with reference to FIG. 3. For example, as depicted in FIG. 6C, the dressing can comprise a wound contact layer 610, a spacer layer 611, a first cover layer 613 positioned above the wound contact layer 610 and spacer layer 611. The pump and electronics package 650 can be positioned above the first cover layer 613. Additionally, the absorbent layer 622 can be positioned above the first cover layer 613 and adjacent to the pump and electronics package 650. In some embodiments, the absorbent layer 622 can include a recess or space to receive the pump and electronics package. A second cover layer 619 can be positioned above the absorbent layer 622 and can seal at the perimeter of the second cover layer 619 to the wound contact layer 610 at the perimeter of the wound contact layer 610. Filter 620 can be located adjacent to the pump and electronics package 650. The filter 620 can be a hydrophobic filter configured to protect the pump and electronics package from exposure to fluid. In some embodiments, the one or more cover layers can be used to enclose the pump and electronics package 650. For example, a third cover layer can be used to incorporate the filter 620 and form a barrier between the fluid in the absorbent layer and/or spacer layer and the pump inlet. Second filter 621 can be located on the second cover layer 619. The second filter can be located at a position adjacent to an outlet or exhaust of the pump system. Additionally or alternatively, the exhaust of the pump can be gaseously connected to the filter 621 positioned proximate to the exhaust. The gaseous connection can include one or more conduits and/or chambers.

In some embodiments, one or more cover layers can be used to form a pouch enclosing the pump and/or electronics package 650. In some embodiments, one or more portions of spacer layer 611 can be included around the first cover layer 613, the pump and electronics package 650, and the absorbent layer 622. Therefore, one or more spacer layer can run along the wound contact layer 610, can be positioned along the edge or height of the dressing, and/or run along the top of the dressing below the second cover layer 619. The one or more portions of the spacer layer 611 can form a pouch around the first cover layer 613, absorbent layer 622, and electronics package 650. A second filter 621 can be incorporated on a second cover layer 619. The second cover layer 619 can be positioned above the spacer layer 611, the absorbent layer 622, and the pump and/or electronics package 650 and can seal at the perimeter to the perimeter of the wound contact layer 610. The second filter 621 can be located at a position adjacent to an outlet or exhaust of the pump system. Additionally or alternatively, the exhaust of the pump can be gaseously connected to the filter 621 positioned proximate to the exhaust. The gaseous connection can include one or more conduits and/or chambers.

FIG. 6D illustrates an embodiment of a wound dressing with pump and electronics package 650 positioned within the dressing. The dressing can include a wound contact layer 610 and spacer layer 611. A moisture vapor permeable film or first cover layer 613 can be positioned above the wound contact layer 610 and the spacer layer 611. The pump and electronics package 650 can be positioned above the first cover layer 613. An absorbent layer 622 can be provided above the pump or electronics package 650. A second cover layer 619 can be positioned above the absorbent layer 622 and can seal at the perimeter of the second cover layer 619 to the wound contact layer 610 at the perimeter of the wound contact layer 610.

In some embodiments, the pump and electronics package 650 can be enclosed in a chamber defined by one or more cover layers. The first cover layer 613 could be positioned above the spacer layer 611 and extend up the edge or height of the dressing as shown in FIG. 6D. That first cover layer can then continue over an upper surface of the pump and electronics package 650 to form a pouch that encloses the pump and electronics package 650, or a separate cover layer may be joined to the first cover layer 613 and extend over the absorbent layer 650 to form the pouch. A filter 620 can be provided between the pump and electronics package 650 and the absorbent layer 622 in the cover layer that is on the upper surface of the pump and electronics package 650, as shown in FIG. 6D. The filter 620 can protect the pump and electronics package 650 from exposure to fluid. An additional filter or second filter 621 can be provided on an exhaust side of the pump, such as on a second moisture vapor permeable film or second cover layer 619, or on another cover layer. The filter 621 can be located at a position adjacent to an outlet or exhaust of the pump system or proximate to the exhaust (and connected to the exhaust via one or more conduits and/or chambers). For example, as is illustrated, a chamber 630 can gaseously connect the pump exhaust and the filter 621. In some embodiments, the chamber 630 can function similar to the chamber 430 of FIG. 4. Additionally or alternatively, the chamber 630 can be configured as a silencer to mute noise produced by the pump.

In some embodiments, the dressing can include one or more ports at a perimeter or along a portion or the entire circumference of the dressing to provide negative pressure from the pump to the highest location (with respect to gravity) of the dressing. The circumference port or ports can be used to bring fluid to the uppermost spacer layer or highest portion of the spacer layer first before being drawn down into the superabsorbent layer and pump. In some embodiments, a full circumference port or multiple circumferential ports can be used. The circumference ports can be used at the perimeter of the wound dressing. This can make the fluid behaviour independent of the direction the dressing is applied in. Without this feature, the capacity can be lower if the port is positioned at the bottom portion of the applied dressing. For example, whether an integrated pump or a remote pump is used, if a dressing is positioned on a patient such that the negative pressure is directed into the dressing at a lower portion (with respect to gravity) of the dressing (such as because the pump is located at the bottom portion of the dressing when applied), the capacity of the dressing may be lower because fluid may tend to pool toward the bottom of the dressing. In some embodiments, multiple ports positioned circumferentially around the dressing, or a single circumferential port, in fluid communication with the negative pressure source, can be used to draw fluid through the spacer layer to higher locations on the dressing. Then, fluid can be drawn downward into the absorbent layer.

In some embodiments, the whole pump pouch as described above can be generated as a specific layer that can be brought into the factory as a reel and/or folded raw material, allowing the manufacture of a full system using the machinery used to manufacture the layers of a wound dressing. The pump and other components can be placed into their respective compartments in the dressing.

In some embodiments, one or more of the following pump additions can be added to the wound dressing with an integrated pump. The pressure sensor can be added onto a substrate of the pump (for example, ceramic substrate). A pressure fuse can be utilized on the pump substrate to discontinue operation of the pump if the pressure generated exceeds an acceptable threshold. Additionally, the pump can be designed for specific pressures. The pump can be designed to disable provision of negative pressure if fluid enters the pump itself.

Figure 7:
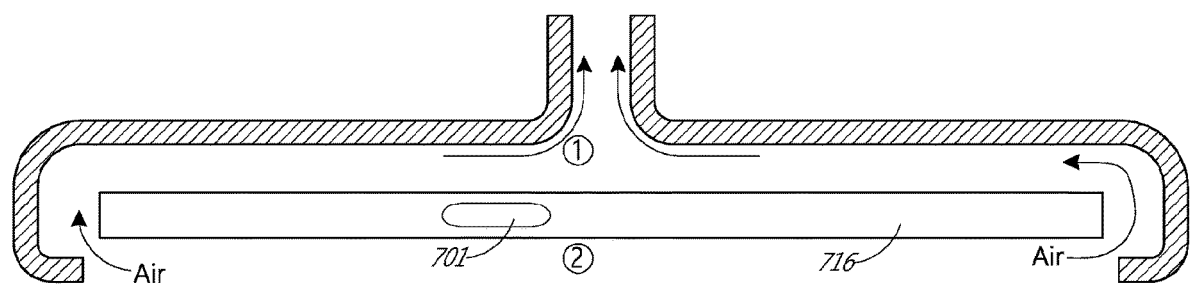
FIG. 7 illustrates an embodiment of a pressure fuse that can be used to discontinue operation of the pump if the pressure exceeds an acceptable (or safe) threshold pressure.

FIG. 7 illustrates a pressure fuse that can be used to discontinue operation of the pump if the pressure exceeds an acceptable (or safe) threshold pressure according to some embodiments. The pump and pressure fuse illustrated in FIG. 7 can be used in combination with or integrated into the pumps described for use in the dressing embodiments described with reference to FIGS. 2-5, 6A-D, 8, and 10-15. As illustrated in FIG. 7, a void or bubble 701 is provided within or adjacent to a piezo element 716 of a pump. The void or bubble 701 includes gas, such as gas stored at a pressure exceeding the operating pressure of the pump. For example, if the pressure at region 2 in FIG. 7 exceeds a pressure threshold (e.g., falls below −200 mmHg or another suitable threshold value), then the void or bubble 701 bursts and thereby stops operation of the pump. For example, if the bubble 701 ruptures, the piezo element will become inoperative and the pump will no longer work. In other embodiments, the wiring to the piezo element or pump can run across the surface of the bubble (and/or inside the bubble). In such embodiment, bursting of the bubble could sever the wire and thereby stop or discontinue operation of the pump. The illustrated and described embodiments are not limited to pumps operated by piezoelectric transducers. For example, a void or bubble can be used to deactivate or render inoperative voice coil pumps, diaphragm pumps, etc.

Further elements can be incorporated into the device to increase the usability of this device. For example, one or more of speaker(s) and/or vibration indicator(s) can be included. The pump can be operated via a controller. One or more user interface elements for operating the pump can be included.

Figure 8:
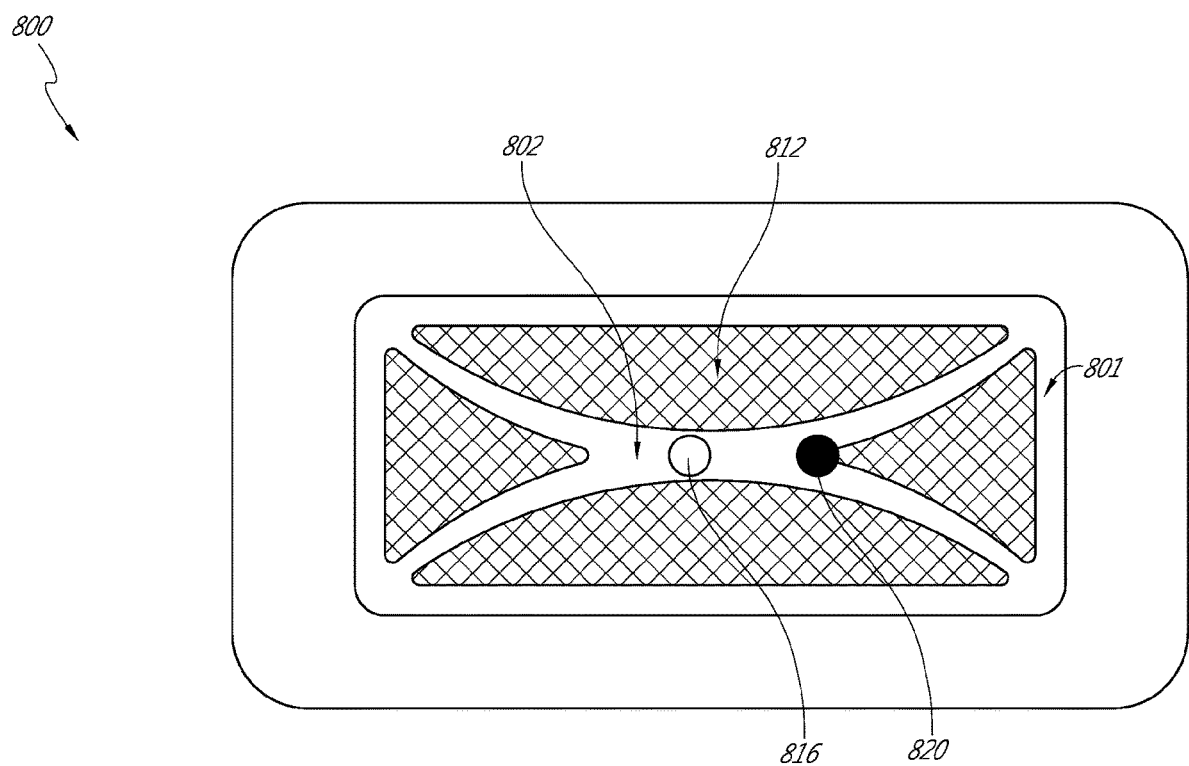
FIG. 8 illustrates an embodiment of an integrated wound dressing with the pump and electronics package incorporated within the dressing.

FIG. 8 illustrates an integrated wound dressing 800 with the pump and electronics package incorporated within the dressing according to some embodiments. The dressing is similar to that described with reference to FIGS. 3-7, except that the dressing 800 includes a different spacer layer and absorbent layer arrangement. From the bottom up, the dressing 800 comprises a wound contact layer, a spacer layer, an absorbent layer or superabsorber 812, and a moisture vapor permeable cover layer. The spacer layer comprises or defines a channel 801 that forms a ring about the wound dressing, and as illustrated forms a ring around the perimeter of the overlying absorbent layer. In some embodiments, the spacer layer has a rectangular shape with a perimeter that is larger than the overlying absorbent layer. Thus, the absorbent layer 812 is surrounded by the spacer channel 801. There are additional channels 802 formed in the absorbent layer that expose the underlying spacer layer when viewed from above. These channels 802 may run diagonally across the rectangular dressing and pass through the middle of the dressing. As illustrated the channels may divide the absorbent layer into four portions. In some embodiments, a pump 816 and/or electronic package may be provided above the moisture vapor permeable cover layer as described in earlier embodiments, and in some embodiments may be positioned in a pouch defined by a first cover layer and optionally a second cover layer over the pump and/or electronics package. In some embodiments, the pump 816 can be positioned in the channels 802 between the portions of the absorbent layer 812. The pump 816 can be positioned on top of and/or embedded in the spacer layer of the channels 802. An outlet port 820 can be provided on the top cover layer of the dressing. In some embodiments, the outlet port 820 can include one or more filters as described in embodiments described herein. When negative pressure is applied to the wound dressing by the pump 816, the channels 801 and 802 form chambers that can facilitate evaporation of fluid.

Figure 9B:
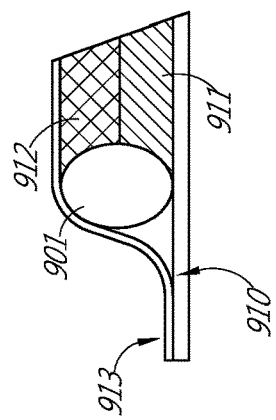
FIGS. 9A-9B illustrate another embodiment of an integrated wound dressing.
Figure 9A:
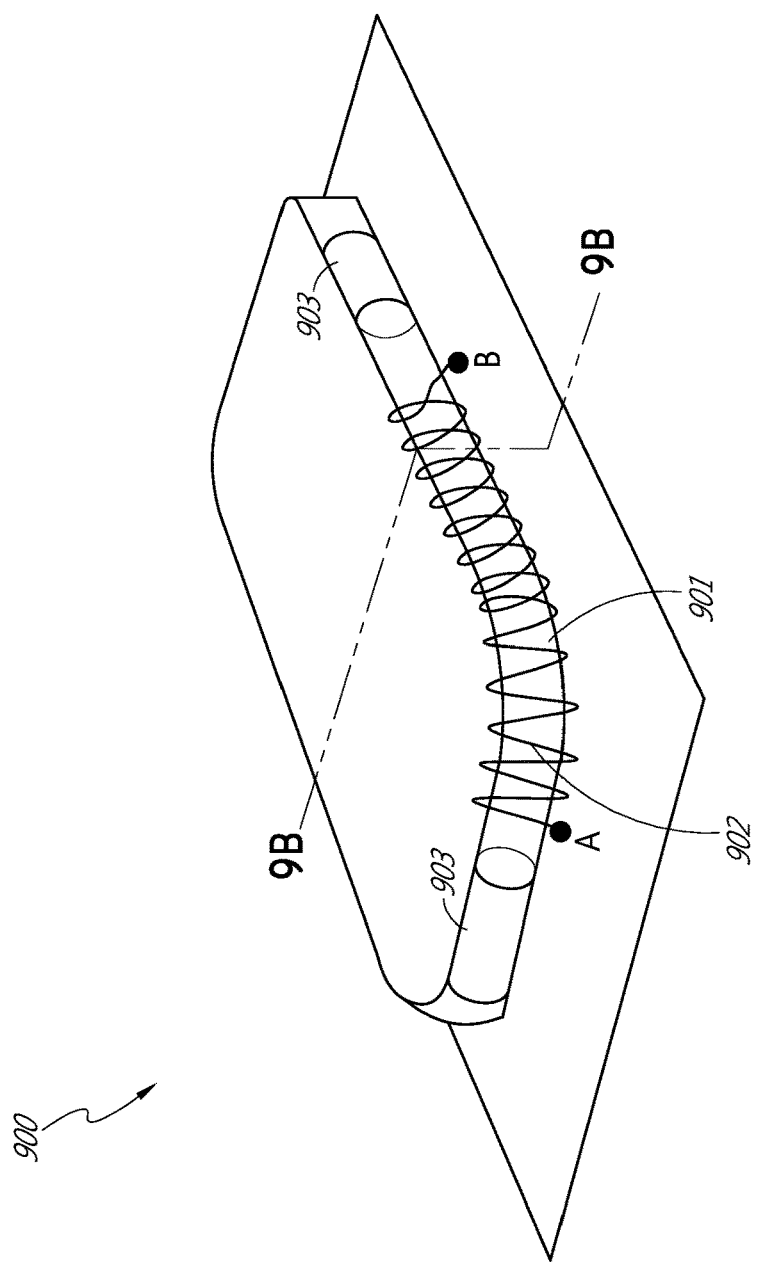

FIGS. 9A-9B illustrate integrated wound dressing 900 according to some embodiments. As with at least some of the earlier described embodiments, the wound dressing 900, from the bottom up, comprises a wound contact layer 910, a spacer layer 911, a superabsorber or absorbent layer 912, and a top film or moisture vapor permeable cover layer 913. As illustrated in FIG. 9A, the integrated wound dressing 900 comprises a tube 901 filled with magnetic fluid 901. As illustrated in FIG. 9B, the tube 901 can be positioned on the perimeter of the spacer layer 911 and/or absorbent layer 912, and the tube 901 can run along or across the dressing 900.

FIG. 9A also illustrates a coil of wire 902 excited by sinusoidal or other potential difference between points A and B. The dressing further comprises one or more pump chambers 903 positioned on the dressing as illustrated in FIG. 9A. Each of the pump chambers 903 can include one or more one-way valves. In some embodiments, the pump chambers can have an additional membrane or piston positioned between the magnetic fluid and chamber. The magnetic fluid can move within the tube due to the excited coil of wire and, in communication with the one-way valves of the pump chamber, can create a negative pressure in the dressing. In some embodiments, the magnetic fluid in the tube can move linearly to the right or to the left depending on the direction of the magnetic field generated by the potential applied to the coil. The pump chambers on either side of the tube can act as intake and exhaust chambers depending of the direction the fluid is moving. In some embodiments, the chambers on either side of the magnetic tube can include a one-way intake and a one-way exhaust valve.

For example, when the magnetic fluid is actuated to move to the left, it could push a piston to force an exhaust valve on the left chamber to open, and at the same time, the leftward movement of the fluid could pull on a piston adjacent the right pump chamber to open an intake valve to allow air to enter the right chamber. Once the direction of the magnetic field was changed, the fluid could move rightward so that the piston on the right could shut the intake valve and open the exhaust valve on the right chamber to exhaust the air, while at the same time the rightward movement of the magnetic liquid would pull on the piston adjacent the left pump chamber to open the intake valve of that chamber to allow air in. In some embodiments, a membrane can be used as an alternative to the piston described previously. The membrane can be flexed in one direction to cause the intake valve to open and flexed in an opposite direction to cause the exhaust valve to open, where the intake and exhaust valves are not open at the same time. Therefore, the tube of magnetic fluid can be a sealed tube.

As shown in FIG. 9B, the wound dressing can include a wound contact layer 910 and a moisture vapor permeable top film or cover layer 913. The perimeter of the cover layer 913 can seal to the perimeter of the wound contact layer enclosing the components of the wound dressing apparatus.

Figure 10:
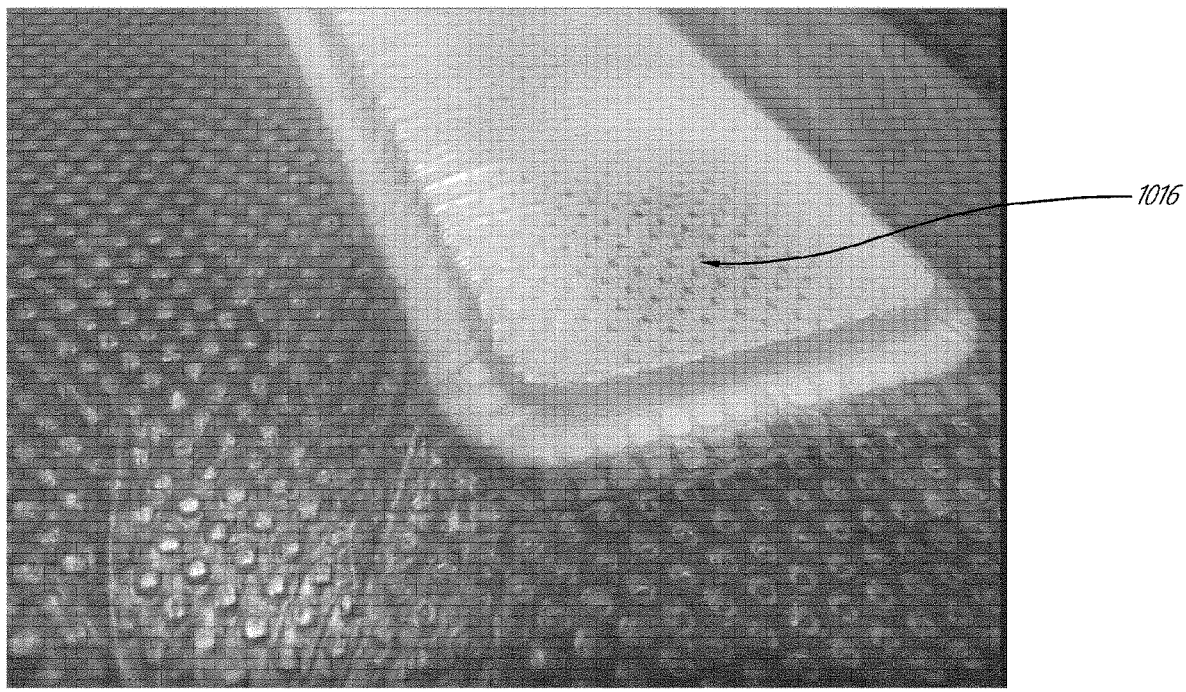
FIG. 10 illustrates a close up view of one end of an embodiment of an integrated wound dressing.
Figure 11:
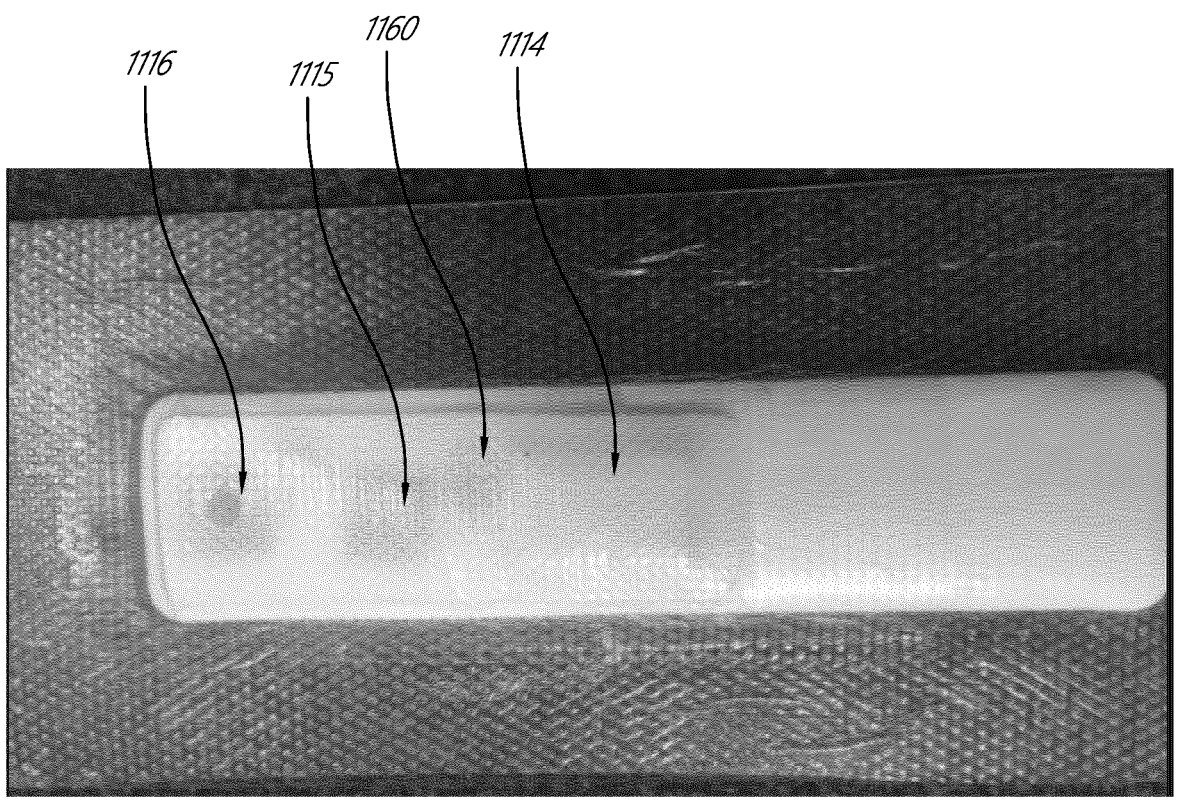
FIG. 11 shows a top view of an embodiment of a wound dressing where the pump and associated components are visible.
Figure 12:
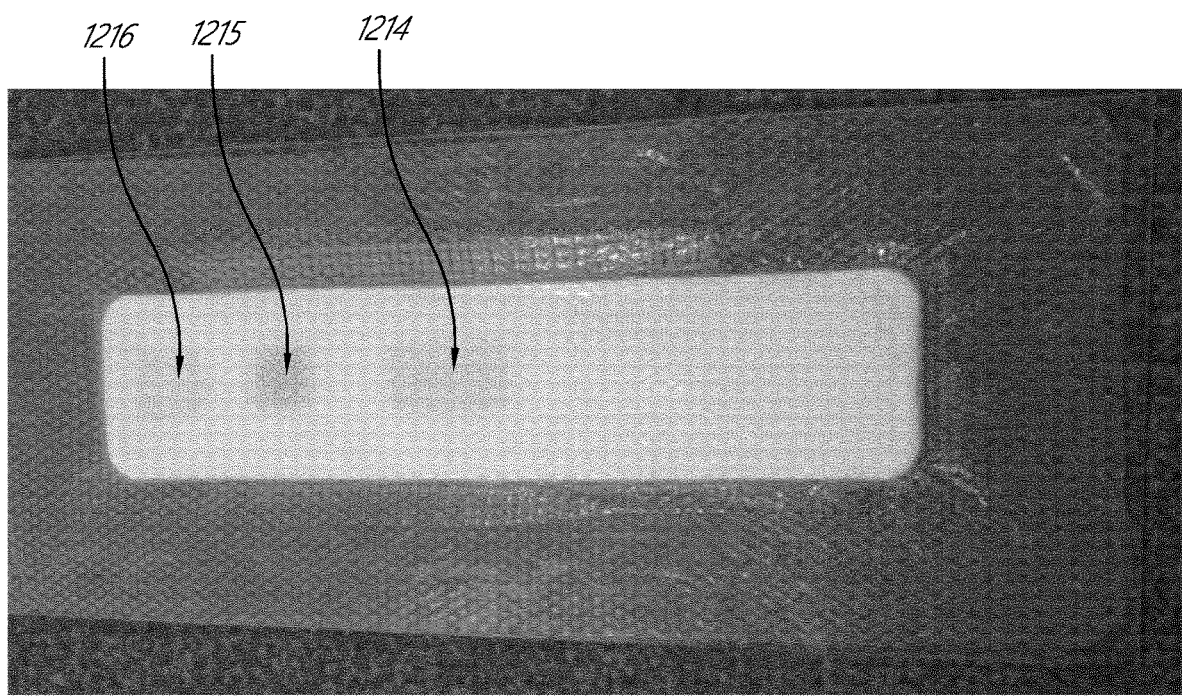
FIG. 12 shows a bottom view of an embodiment of a wound dressing where recesses for the pump and associated components are visible.

FIGS. 10-12 show embodiments of integrated dressings. FIG. 10 illustrates a close up view of one end of the wound dressing in an embodiment where a pump is positioned between two cover layers and/or positioned in a pouch similar to the embodiments described with reference to FIGS. 1-5 and 6A-6D. The pump can also be embedded in a layer of spacer material or absorbent material. The pump 1016 is visible as a dark spot under the top layer.

FIG. 11 shows a top view of a wound dressing where the pump and associated components are visible in a wound dressing embodiment similar to the dressings described with reference to FIGS. 1-5 and 6A-6D. The dressing can have the pump and associated components positioned between two cover layers and they can be embedded in a recess of a spacer layer and/or absorbent layer as described herein. The pump 1116, electronics package 1115, switch 1160 for operating the pump (e.g., turning the pump on/off), and power source 1114 are visible from the top of the dressing.

FIG. 12 shows a bottom view of a wound dressing where recesses for the pump and associated components are visible in a wound dressing embodiment similar to the dressings described with reference to FIGS. 1-5 and 6A-6D. The dressing can have the pump and associated components positioned between two cover layers and they can be embedded in a recess of a spacer layer and/or absorbent layer as described herein. Recess 1216 can be a pump recess, recess 1215 can be an electronics package recess, and recess 1214 can be a power source recess.

Figure 13:
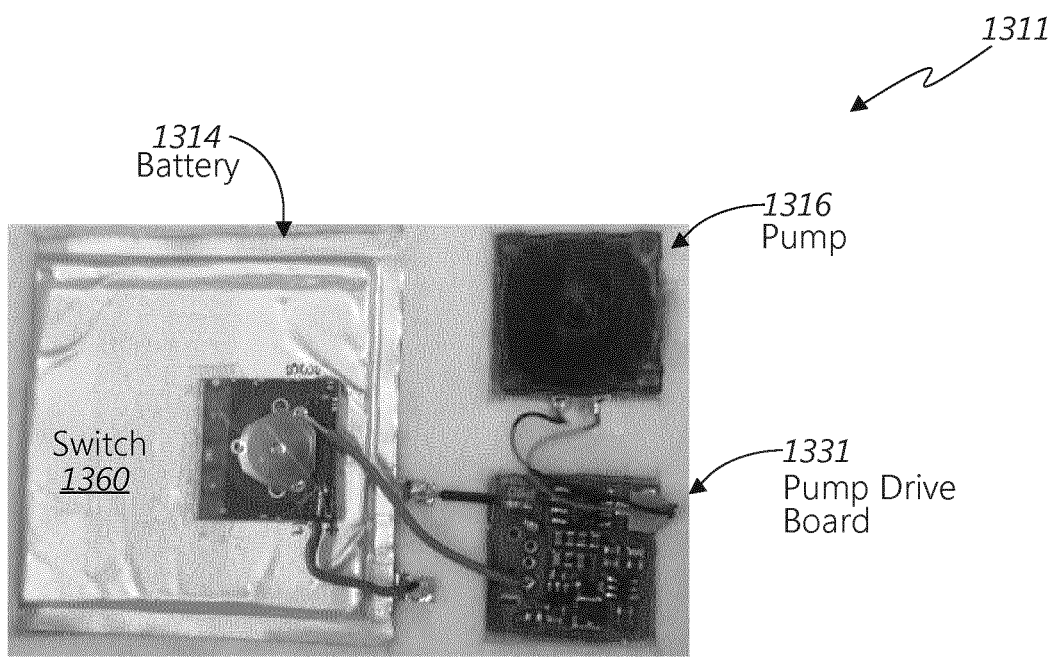
FIGS. 13-15 shows an embodiment a wound dressing with integrated electronic components.
Figure 14:
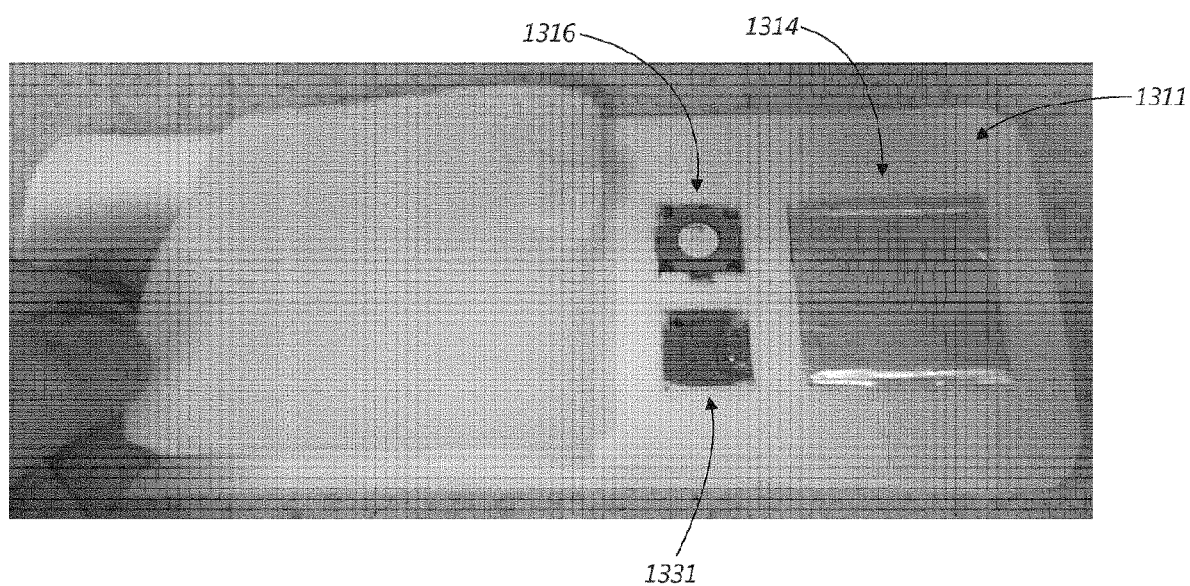
Figure 15:
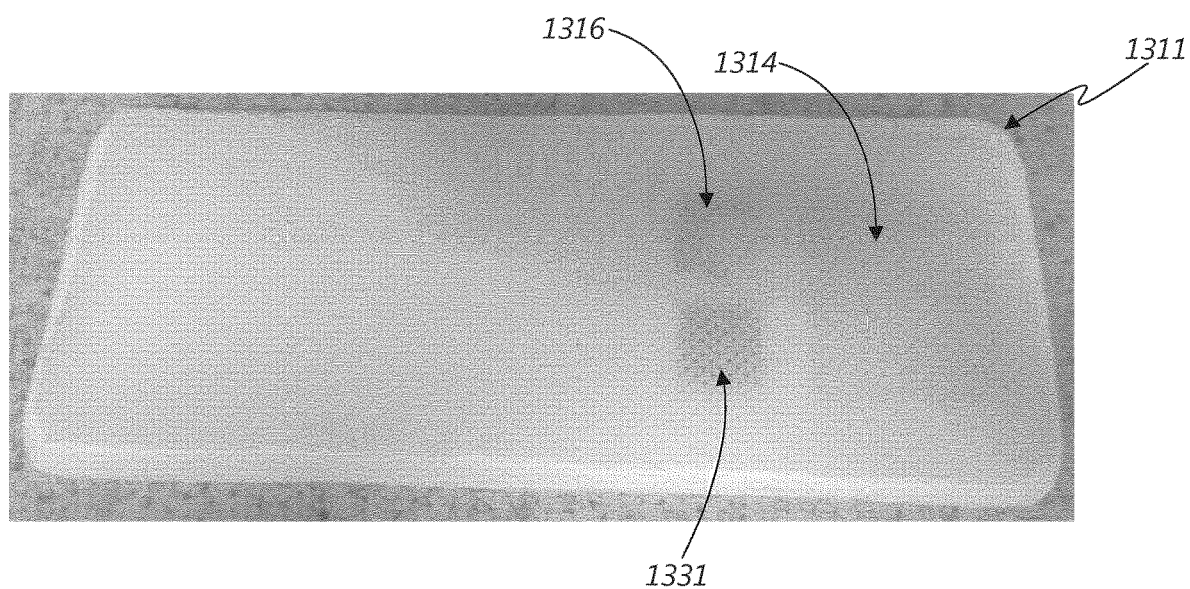

FIGS. 13-15 show an embodiment of a wound dressing with integrated electronic components similar to the dressings described with reference to FIGS. 1-5 and 6A-6D. The dressing can have the pump and associated components positioned between two cover layers and they can be embedded in a recess of a spacer layer and/or absorbent layer as described herein. The dressing of FIGS. 13-15 include a pump 1316, pump drive board 1331, battery 1314, and switch 1360 arranged on spacer layer 1311. In some embodiments, the switch 1360 can be arranged on and/or in the electronics package or provide in a recess.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein.

Certain embodiments of the disclosure are encompassed in the claims presented at the end of this specification, or in other claims presented at a later date. Additional embodiments are encompassed in the following set of numbered embodiments:

Embodiment 1

A wound dressing apparatus comprising:
a wound contact layer configured to be positioned in contact with a wound;
a first spacer layer;
an absorbent layer;
a first cover layer configured to cover and form a seal over the wound contact layer, the first spacer layer, and the absorbent layer, wherein the first cover layer comprises a first filter;
a negative pressure source configured to be positioned above the first cover layer;
a second spacer;
a second cover layer configured to cover and form a seal over the negative pressure source and second spacer, wherein the second cover layer comprising a second filter;
wherein the absorbent layer comprises at least one recess configured to receive the negative pressure source; and
wherein the first filter of the first cover layer is configured to align with one of the at least one recesses of the absorbent layer.

Embodiment 2

The wound dressing apparatus of Embodiment 1, wherein the second cover layer is configured to seal to the first cover layer.

Embodiment 3

The wound dressing apparatus of any of Embodiments 1-2, wherein the negative pressure source comprises a piezoelectric pump.

Embodiment 4

The wound dressing apparatus of any of Embodiments 1-3, further comprising one or more user interface components configured to allow a user to operate the negative pressure source.

Embodiment 5

The wound dressing apparatus of any of Embodiments 1-4, further comprising a switch configured to activate the electronics in the dressing, wherein the switch is incorporated into the dressing.

Embodiment 6

The wound dressing apparatus of any of Embodiments 1-5, further comprising a chamber configured to store at least some gas exhausted by the negative pressure source, thereby increasing rate of evaporation of moisture.

Embodiment 7

A wound dressing apparatus comprising:
- a wound contact layer configured to be positioned in contact with a wound;
- a spacer layer;
- a first absorbent layer;
- a first cover layer configured to cover and form a seal over the wound contact layer, the spacer layer, and the first absorbent layer, wherein the first cover layer comprises a first filter;
- a negative pressure source configured to be positioned above the first cover layer;
- a second filter in communication with the exhaust of the negative pressure source;
- a second cover layer configured to cover and form a seal over the negative pressure source and the second filter, and the second cover layer comprising a third filter; and
- wherein the first filter of the first cover layer is configured to align with an inlet of the negative pressure source.

Embodiment 8

The wound dressing apparatus of Embodiment 7, further comprising a chamber configured to store at least some gas exhausted by the negative pressure source, thereby increasing rate of evaporation of moisture.

Embodiment 9

The wound dressing apparatus of any of Embodiments 7-8, further comprising a second absorbent layer, wherein the second absorbent layer positioned between the first cover layer and the second cover layer.

Embodiment 10

The wound dressing apparatus of any of Embodiments 7-9, wherein the second absorbent layer is configured to draw fluid through the first cover layer.

Embodiment 11

The wound dressing apparatus of any of Embodiments 7-10, wherein the second cover layer is configured to seal to the first cover layer.

Embodiment 12

The wound dressing apparatus of any of Embodiments 7-11, wherein the negative pressure source comprises a piezoelectric pump.

Embodiment 13

A wound dressing apparatus comprising:
- a wound contact layer configured to be positioned in contact with a wound;
- a spacer layer;
- an absorbent layer;
- a first cover layer configured to cover and form a seal over the wound contact layer, the spacer layer, and the absorbent layer, wherein the first cover layer comprises a first filter;
- a negative pressure source configured to be positioned above the first cover layer;
- a second filter in communication with the exhaust of the negative pressure source; and
- at least one ultrasonic oscillator, wherein the ultrasonic oscillator is configured to atomize water from the absorbent layer.

Embodiment 14

The wound dressing apparatus of Embodiment 13, further comprising a second cover layer configured to cover and form a seal over the negative pressure source, the second filter, and the at least one ultrasonic oscillator.

Embodiment 15

The wound dressing apparatus of any of Embodiments 13-14, wherein the first filter of the first cover layer is configured to align with an inlet of the negative pressure source.

Embodiment 16

The wound dressing apparatus of any of Embodiments 13-15, wherein the second cover layer is configured to seal to the first cover layer.

Embodiment 17

The wound dressing apparatus of any of Embodiments 13-16, wherein the negative pressure source comprises a piezoelectric pump.

Embodiment 18

The wound dressing apparatus of any of Embodiments 13-17, further comprising one or more user interface components configured to allow a user to operate the negative pressure source.

Embodiment 19

A wound dressing apparatus comprising:
- a wound contact layer configured to be positioned in contact with a wound;
- a spacer layer;
- an absorbent layer;
- a first cover layer configured to cover and form a seal over the wound contact layer, the spacer layer, and the absorbent layer, wherein the first cover layer comprises a first filter;
- a negative pressure source configured to be positioned above the first cover layer;
- a second cover layer configured to cover and form a seal over the negative pressure source, the second cover layer comprising a second filter;
- wherein the first filter of the first cover layer is configured to be in communication with an inlet in the negative pressure source and the second filter of the second cover layer is configured to be in communication with an exhaust of the negative pressure source.

Embodiment 20

The wound dressing apparatus of Embodiment 19, wherein the absorbent layer comprises at least one recess configured to receive the negative pressure source.

Embodiment 21

The wound dressing apparatus of any of Embodiments 19-20, wherein the second cover layer is configured to seal to the first cover layer.

Embodiment 22

A wound dressing apparatus comprising:
- a wound contact layer configured to be positioned in contact with a wound;
- a spacer layer;
- an absorbent layer;
- a negative pressure source configured to be in fluid communication with the wound;
- a first cover layer configured to cover and form a seal around the negative pressure source, wherein the first cover layer comprises a first filter; and
- a second cover layer configured to cover and form a seal over the absorbent layer, spacer layer, first cover layer with the negative pressure source, the second cover layer comprising a second filter;
- wherein the first filter of the first cover layer and the second filter of the second cover layer are configured to be in communication with the negative pressure source.

Embodiment 23

The wound dressing apparatus of Embodiment 22, wherein the second cover layer is configured to seal at a perimeter of the second cover layer to the wound contact layer at a perimeter of the wound contact layer.

Embodiment 24

The wound dressing apparatus of any of Embodiments 22-23, wherein the first cover layer forms a pouch around the negative pressure source, wherein the first cover layer comprises one or more cover layers combined to form the pouch or one single cover layer to form the pouch and wherein the first cover layer pouch comprises an interior surface comprising a surface facing the negative pressure source and an exterior surface opposite the interior surface.

Embodiment 25

The wound dressing apparatus of any of Embodiments 22-24, wherein the spacer layer comprises one or more portions configured to be positioned around the exterior surface of the first cover layer.

Embodiment 26

The wound dressing apparatus of any of Embodiments 22-25, wherein the spacer layer is positioned between the wound contact layer and the first cover layer pouch and the absorbent layer is positioned between the first cover layer pouch and the second cover layer.

Embodiment 27

A wound dressing apparatus comprising:
- a wound dressing comprising:
  - a first cover layer configured to cover and form a seal over the wound forming a negative pressure reservoir between the wound and the first cover layer;
  - a negative pressure source configured to provide negative pressure to the reservoir; and
  - a void within or adjacent to the negative pressure source, wherein the void comprises gas at a predefined pressure, wherein the void is configured to burst and thereby stop operation of the negative pressure source when the pressure in the reservoir exceeds a pressure threshold.

Embodiment 28

The wound dressing apparatus of Embodiment 27, wherein the negative pressure source comprises a piezoelectric pump.

Embodiment 29

The wound dressing apparatus of Embodiment 28, wherein the void is in communication with an electrical wiring of the piezoelectric pump and bursting of the void causes the electrical wiring to be severed.

Embodiment 30

The wound dressing apparatus of any of Embodiments 27-29, further comprising:
- a wound contact layer configured to be positioned in contact with a wound;
- a spacer layer; and
- an absorbent layer, wherein the first cover layer is configured to cover and form a seal over the wound contact layer, the spacer layer, and the absorbent layer.

Embodiment 31

The wound dressing apparatus of any of Embodiments 27-30, further comprising a second cover layer configured to cover and form a seal over the negative pressure source, the second cover layer configured to seal to the first cover layer.

Embodiment 32

The wound dressing apparatus of any of Embodiments 27-31, further comprising one or more user interface components configured to allow a user to operate the negative pressure source.

Embodiment 33

A wound dressing apparatus comprising:
a wound contact layer configured to be positioned in contact with a wound;
a spacer layer;
an absorbent layer;
one or more channels defined by the spacer layer around a perimeter of the absorbent layer and between portions of the absorbent layer extending across a middle of the absorbent layer; and
a negative pressure source positioned in one of the channels.

Embodiment 34

A wound dressing apparatus comprising:
a wound contact layer configured to be positioned in contact with a wound;
a spacer layer;
an absorbent layer;
a cover layer configured to cover and form a seal over the wound contact layer, the spacer layer, and the absorbent layer forming a negative pressure reservoir;
a negative pressure source configured to be positioned within the wound dressing, the negative pressure source comprising:
a tube positioned on the perimeter of the spacer layer and/or absorbent layer, the tube comprising a magnetic fluid and a coiled wire configured to be excited by potential differences between two points of the tube; and
one or more pump chambers positioned in the tube, wherein the one or more pump chambers comprise one or more one-way valves.

Embodiment 35

The wound dressing apparatus of Embodiment 34, wherein the one or more pump chambers comprise a membrane or piston positioned between the magnetic fluid and chamber.

Embodiment 36

The wound dressing apparatus of any of Embodiments 34-35, wherein the one or more pump chambers are positioned on either side of the magnetic tube.

Embodiment 37

The wound dressing apparatus of any of Embodiments 34-36, wherein the one or more pump chambers comprise a one-way intake and a one-way exhaust valve.

Embodiment 38

The wound dressing apparatus of any of Embodiments 34-37, wherein the intake and exhaust valves are not open at the same time creating a sealed tube of magnetic fluid.

What is claimed is:
1. A wound dressing apparatus comprising:
a wound contact layer configured to be positioned in contact with a wound;
a first cover layer positioned over the wound contact layer;
one or more spacer layers positioned between the wound contact layer and the first cover layer, wherein a spacer layer is positioned on an upper surface of the wound contact layer;
a first absorbent layer positioned over the spacer layer positioned on the upper surface of the wound contact layer;
a negative pressure source configured to be in fluid communication with the wound, the negative pressure source configured to draw wound fluid through the one or more spacer layers into the first absorbent layer, wherein the negative pressure source is located in:
a recess of a spacer layer or the first absorbent layer; and
a pocket or chamber defined at least in part by the first cover layer and a second sealing layer; and
a first filter provided in a flow path between the negative pressure source and the wound contact layer;
wherein the first cover layer is configured to form a seal over the first absorbent layer and the one or more spacer layers and is sealed to the wound contact layer; and
wherein the second sealing layer seals the negative pressure source; and
a spacer layer or second absorbent layer between the first cover layer and the second sealing layer.
2. The wound dressing apparatus of claim 1, wherein the negative pressure source is located in a recess in the first absorbent layer.
3. The wound dressing apparatus of claim 1, wherein the first absorbent layer is positioned between the wound contact layer and the first cover layer.
4. The wound dressing apparatus of claim 1, wherein the first filter is located in the first cover layer.
5. The wound dressing apparatus of claim 1, wherein a second filter in the second sealing layer.
6. The wound dressing apparatus of claim 1, wherein the first cover layer is positioned on an upper surface of the first absorbent layer.
7. The wound dressing apparatus of claim 1, comprising one or more ultrasonic oscillators.
8. The wound dressing apparatus of claim 1, wherein the one or more spacer layers comprise a recess or pouch for receiving the first absorbent layer and/or the negative pressure source.
9. The wound dressing apparatus of claim 1, wherein the negative pressure source is positioned beneath the first absorbent layer.

10. The wound dressing apparatus of claim 1, comprising a pressure fuse configured to discontinue operation of the negative pressure source if the pressure exceeds a threshold pressure.

11. The wound dressing apparatus of claim 1, further comprising a tube filled with magnetic fluid for creating negative pressure in the apparatus.

12. The wound dressing apparatus of claim 1, wherein electronic components associated with the negative pressure source are positioned in separate recesses within the absorbent layer and/or spacer layers.

13. A wound dressing apparatus comprising:
a wound contact layer configured to be positioned in contact with a wound;
a first cover layer positioned over the wound contact layer;
one or more spacer layers positioned between the wound contact layer and the first cover layer, wherein a spacer layer is positioned on an upper surface of the wound contact layer;
an absorbent layer positioned over the spacer layer positioned on the upper surface of the wound contact layer;
a negative pressure source configured to be in fluid communication with the wound, the negative pressure source configured to draw wound fluid through the one or more spacer layers into the absorbent layer, wherein the negative pressure source is located in:
a recess of a spacer layer or the absorbent layer; and
a pocket or chamber defined at least in part by the first cover layer and a second sealing layer; and
a first filter provided in a flow path between the negative pressure source and the wound contact layer;
wherein the first cover layer is configured to form a seal over the absorbent layer and the one or more spacer layers and is sealed to the wound contact layer; and
wherein the second sealing layer seals the negative pressure source; and
a third cover layer positioned over the second sealing layer, the third cover layer defining a chamber between the second sealing layer and the third cover layer.

14. The wound dressing apparatus of claim 13, further comprising a further absorbent and/or spacer layer within the chamber defined between the second sealing layer and the third cover layer.

15. The wound dressing apparatus of claim 13, further comprising a third filter in the third cover layer.

16. A wound dressing apparatus comprising:
a wound contact layer configured to be positioned in contact with a wound;
a first cover layer positioned over the wound contact layer;
one or more spacer layers positioned between the wound contact layer and the first cover layer, wherein a spacer layer is positioned on an upper surface of the wound contact layer;
an absorbent layer positioned over the spacer layer positioned on the upper surface of the wound contact layer, wherein the dressing comprises channels around a perimeter of the absorbent layer and across a middle of the absorbent layer to expose portions of an underlying spacer layer;
a negative pressure source configured to be in fluid communication with the wound, the negative pressure source configured to draw wound fluid through the one or more spacer layers into the absorbent layer, wherein the negative pressure source is located in:
a recess of a spacer layer or the absorbent layer; and
a pocket or chamber defined at least in part by the first cover layer and a second sealing layer; and
a first filter provided in a flow path between the negative pressure source and the wound contact layer;
wherein the first cover layer is configured to form a seal over the absorbent layer and the one or more spacer layers and is sealed to the wound contact layer; and
wherein the second sealing layer seals the negative pressure source.

* * * * *